United States Patent [19]

Duggan

[11] Patent Number: 5,092,330
[45] Date of Patent: Mar. 3, 1992

[54] ANALOG TO DIGITAL CONVERTER

[75] Inventor: Stephen R. Duggan, Rosemount, Minn.

[73] Assignee: Medtronic, Inc., Minneapolis, Minn.

[21] Appl. No.: 436,460

[22] Filed: Oct. 12, 1989

Related U.S. Application Data

[60] Division of Ser. No. 127,308, Mar. 5, 1980, Pat. No. 4,958,632, which is a continuation-in-part of Ser. No. 926,303, Jul. 20, 1978, abandoned.

[51] Int. Cl.$^5$ .............................................. A61B 1/00
[52] U.S. Cl. ............................. 128/630; 128/419 PG; 341/157
[58] Field of Search ............... 341/155, 157, 158, 166; 328/134, 150; 377/121, 126; 128/630

[56] References Cited

U.S. PATENT DOCUMENTS

| | | | |
|---|---|---|---|
| 3,500,196 | 3/1970 | Cooper | 341/157 |
| 3,668,690 | 6/1972 | Ormond | 341/157 |
| 3,899,691 | 8/1975 | Hama | 377/121 |
| 4,008,405 | 2/1977 | Neumann et al. | 341/157 |
| 4,061,030 | 12/1977 | Griverus | 341/157 |
| 4,357,599 | 11/1982 | Takahashi | 341/157 |

Primary Examiner—William E. Kamm
Attorney, Agent, or Firm—Reed A. Duthler

[57] ABSTRACT

A multi-mode, adaptable, implantable pacemaker is described including a microprocessor and memory programmed or capable of being programmed with a variety of processes for stimulating the patient's heart and/or for sensing and transmitting to a device external of the patient's body, various conditions of or activities of the patient's heart, or conditions of the pacemaker itself. The pacemaker includes a multiplexer by which a variety of analog and digital inputs are accessed under the control of the microprocessor and operated upon by the processes stored in the memory and executed by the microprocessor. The output of the pacemaker comprises a plurality of latch drivers and switches, which are selectively operable to apply stimulation to the patient's heart, as well as to sense signals indicative of the patient's heart activity as well as other internal conditions. The pacemaker is capable of transmitting these signals via a link such as an RF or acoustical link to an external monitoring apparatus. The external apparatus may transmit code signals to be received by the pacemaker, whereby the pacemaker's memory may be reprogrammed, dependent upon change of the patient's condition. Illustratively, the memory is divided into a plurality of blocks and control signals may be sent from the external apparatus to address the initial or starting location within another block, whereby another, selected program or process may be executed by the microprocessor.

5 Claims, 4 Drawing Sheets

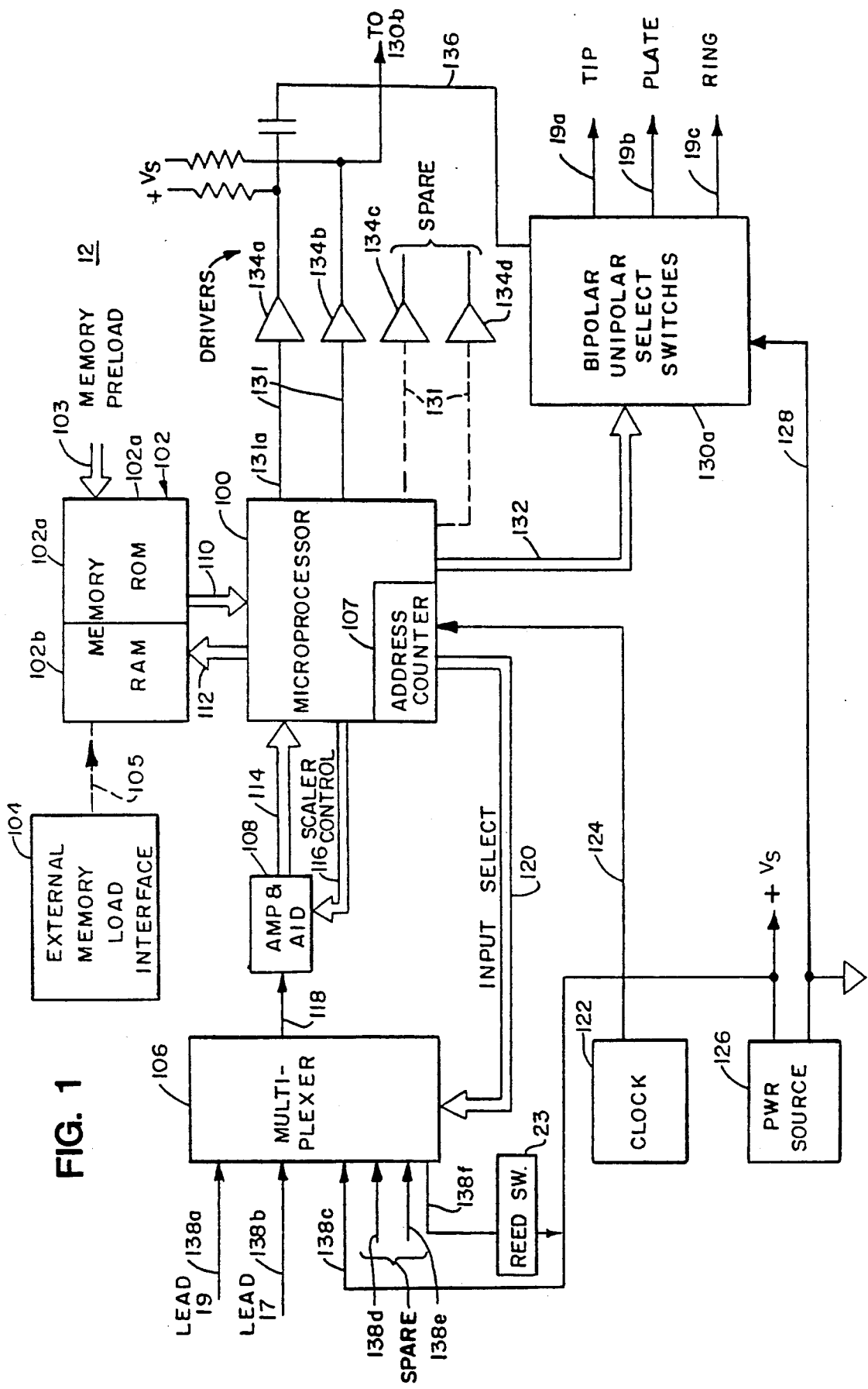

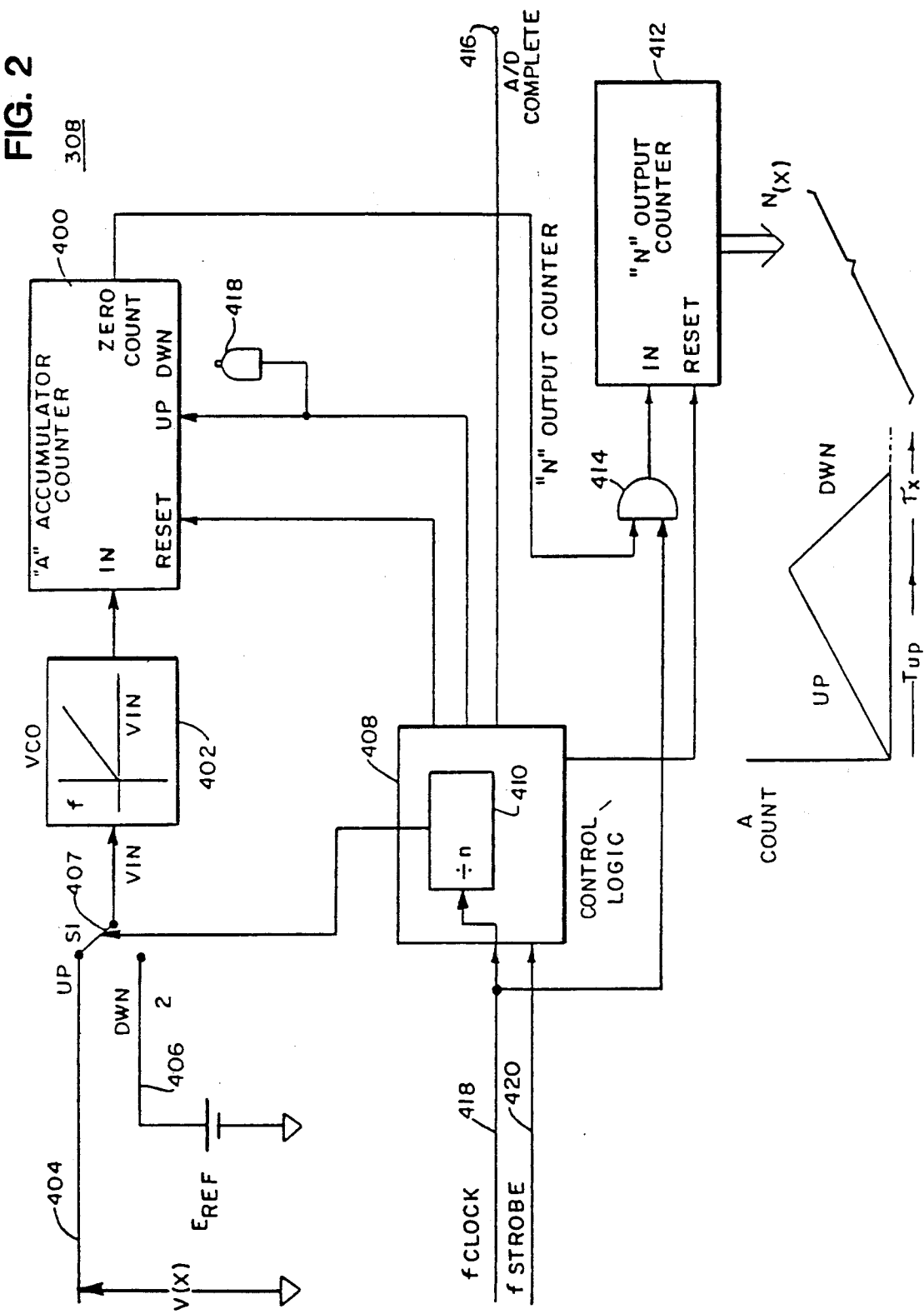

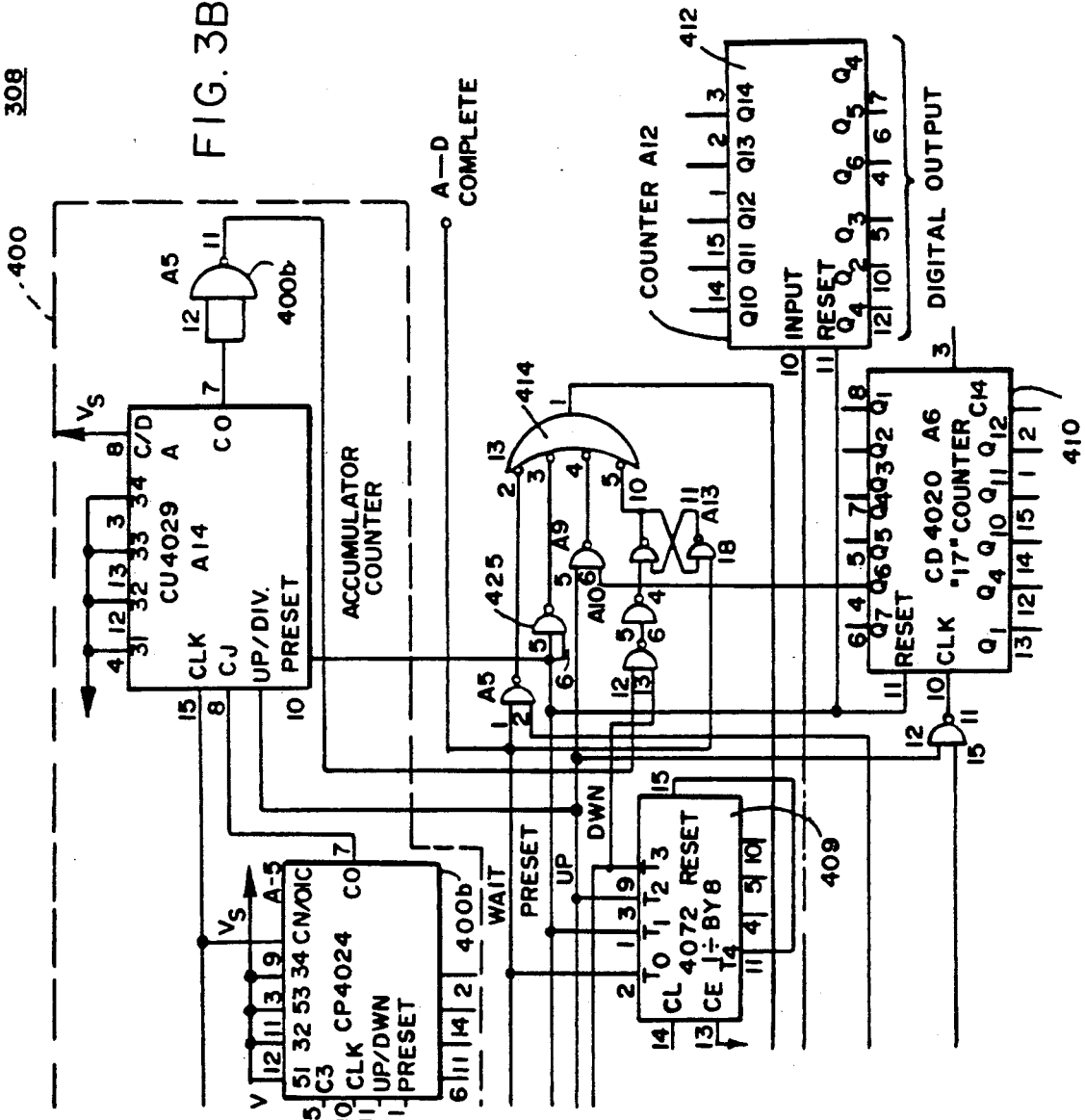

ANALOG TO DIGITAL CONVERTER

RELATED U.S. APPLICATION DATA

This application is a division of U.S. application Ser. No. 127,308 filed Mar. 5, 1980, now issued as U.S. Pat. No. 4,958,632, which in turn was a continuation-in part of U.S. application Ser. No. 926,303, filed July 20, 1978 now abandoned.

BACKGROUND OF THE INVENTION

1. Field of the Invention

This invention relates to internally implanted electronic devices adapted to be operated in a variety of modes for stimulating body tissue or to monitor various conditions of the device itself or of body tissue, e.g., the patient's heart. More particularly, the present invention relates to an analog to digital converter particularly optimized for use in conjunction with implantable, battery powered electronic devices such as cardiac pacemakers.

2. Description of the Prior Art

Heart pacers such as that described in U.S. Pat. No. 3,057,356 issued in the name of Wilson Great-batch and assigned to the assigned of this invention, are known for providing electrical stimulus to the heart whereby it is contracted at a desired rate in the order of 72 beats per minute. Such a heart pacemaker is capable of being implanted within the human body and operative in such an environment for long periods of time. Typically, such pacemakers are implanted in the pectoral region or in the abdominal region of the patient by a surgical procedure, whereby an incision is made in such region and the pacemaker with its own internal power supply, is inserted within the patient's body. This pacer operates asynchronously to provide fixed-rate stimulation not automatically changed in accordance with the body's needs, and has proven effective in alleviating the symptoms of complete heart block. An asynchronous pacer, however, has the possible disadvantage of competing with the natural, physiological pacemaker during episodes of normal sinus condition.

An artificial pacer of the demand type has been developed wherein the artificial stimuli are initiated only when required and subsequently can be eliminated when the heart returns to the sinus rhythm. Such a demand pacer is shown in U.S. Pat. No. 3,478,746 issued Nov. 18, 1969 and entitled "CARDIAC IMPLANTABLE DEMAND PACEMAKER". The demand pacer solves the problem arising in asynchronous pacers by inhibiting itself in the presence of ventricular activity (the ventricle's R wave), but by coming "on line" and filling in missed heartbeats in the absence of ventricular activity.

One area where cardiac pacing technology has lagged behind conventional state of electronic technology involves utilization of digital electrical circuits. One reason for this has been the high energy required to operate digital circuits. However, with more recent technology advances in complimentary metal oxide semiconductor (CMOS) devices fabricated on large scale integrated circuits, together with the improvements of cardiac pacemaker batteries, digital electronic circuits are beginning to be utilized in commercial pacemakers. The inherent advantages of digital circuits are their accuracy, and reliability. Typically, the digital circuit is operated in response to a crystal oscillator which provides a very stable frequency over extended periods of time. There have been suggestions in the prior art for utilizing digital techniques in cardiac stimulators and pacemakers since at least 1966. For instance, see the article by Leo F. Walsh and Emil Moore, entitled "Digital Timing Unit for Programming Biological Stimulators" in *The American Journal of Medical Electronics*, First Quarter, 1977, Pages 29 through 34. The first patent suggesting digital techniques is U.S. Pat. No. 3,557,796 in the name of John W. Keller, Jr., et al, and is entitled "Digital Counter Driven Pacer", which issued in 1971.

Other patents disclosing digital techniques useful in cardiac pacing include U.S. Pat. Nos. 3,631,860 in the name of Michael Lopin entitled "Variable Rate Pacemaker, Counter-Controlled, Variable Rate Pacer"; 3,857,399 in the name of Fred Zacouto entitled "Heart Pacer"; 3,865,119 in the name of Bengt Svensson and Gunnar Wallin entitled "Heartbeat Accentuated with Controlled Pulse Amplitude"; 3,870,050 in the name of Wilson Greatbatch entitled "Demand Pacer"; 4,038,991 in the name of Robert A. Walters entitled "Cardiac Pacer with Rate Limiting Means"; 4,043,347 in the name of Alexis M. Renirie entitled "Multiple-Function Demand Pacer with Low Current Drain"; 4,049,003 in the name of Robert A. Walters et al entitled "Digital Cardiac Pacer"; and 4,049,004 in the name of Robert A. Walters entitled "Implantable Digital Cardiac Pacer Having Externally Selectable Operating Parameters and One Shot Digital Pulse Generator for Use Therein".

It is well recognized in the art that the complexity of the circuit incorporated within an internally implanted device is limited by many factors including the drain imposed upon the battery and therefore the expected life of a battery before a surgical procedure is required to replace the device's power source, e.g., a battery.

SUMMARY OF THE INVENTION

It is an object of the present invention to provide an analog to digital converting apparatus. The A/D converter is implemented in CMOS Technology, in order to impose a minimum current drain. The A/D converter circuitry is controlled by means of clock pulses, but is configured such that the output signal from the A/D converter reflects the analog output signal to the A/D converter, independent of the frequency of the clock signal applied to the A/D converter.

Because of its low current drain and its insensitivity to the frequency of the clock signal, the A/D converter of the present invention is particularly desirable for incorporation in implantable devices, such as cardiac pacemakers.

BRIEF DESCRIPTION OF THE DRAWINGS

These and other objects and advantages of the present invention will become more apparent by referring to the following detailed description and accompanying drawings, in which:

FIG. 1 is a functional block diagram of an internally implanted pacemaker, embodying the present invention;

FIG. 2 is a functional block diagram of the A/D converter of the present invention as incorporated within the pacemaker of FIG. 1;

FIGS. 3A and 3B are more detailed circuit diagrams of the A/D converter shown in FIG. 2.

DETAILED DESCRIPTION OF THE PREFERRED EMBODIMENTS OF THIS INVENTION

Figure 3A:
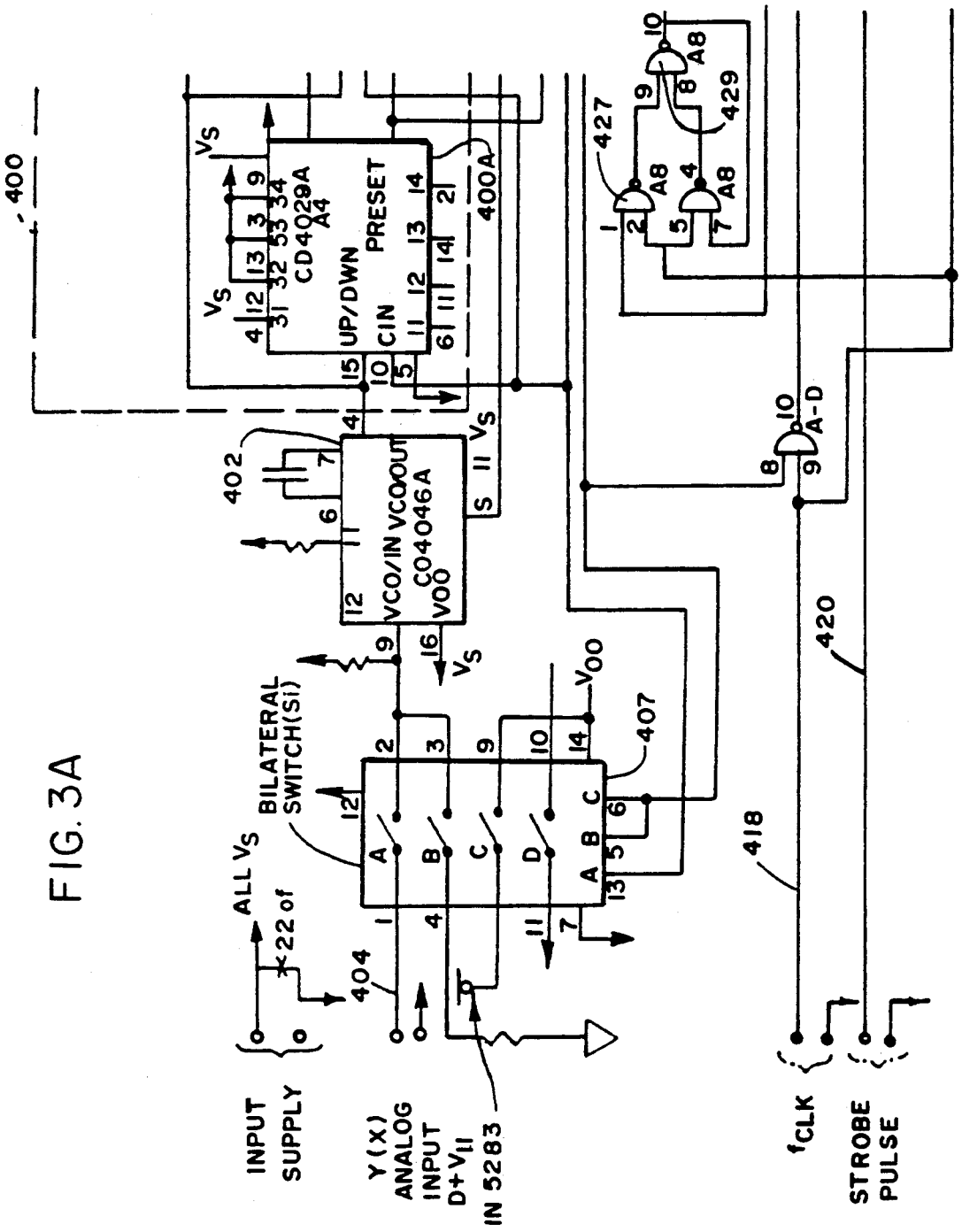

With reference to FIG. 1, there is shown a functional block diagram of a pacemaker, which includes as its central control element a microprocessor 100, and a multiplexer 106 for receiving analog data from a first input 138a coupled via the first lead 19 to the patient's ventricle and a second input 138b coupled via the second lead 17 to the patient's atrium. These various analog (and digital) inputs are selected by the multiplexer 106 under the control of the microprocessor 100 in a selected manner and processed according to processes or programs stored in the memory 102.

In addition, the microprocessor 100 is coupled by an address bus 112 to memory 102, whereby addresses as stored and incremented by an address counter 107 are applied to address selected locations within the memory 102. The addressed data is transferred from the memory 102 via data bus 110 to the microprocessor 100.

In addition, there are additional inputs 138c, d, e and f of the multiplexer 106. The microprocessor 100 provides control signals via an input select bus 120 to the multiplexer 106, whereby one of the inputs 138a to f is selected for application via the conduit 118, a scaling amplifier and analog to digital (A/D) converter 108 and the bus 114 to the microprocessor 100. As suggested in FIG. 1, the output voltage $V_s$ of a power source 126 is coupled via input 138c to the multiplexer 106 in order to appropriately modify the pacer performance as a function of power source variations. For example, it is desired to increase the pacing pulse width as supply voltage decreases to create a more constant energy pulse, or to slow the pacing rate as supply voltage decreases to indicate a need for pacer replacement or modification via external programming. The spare inputs 138d and 138e may be coupled illustratively also to the ventricle and the atrium in order to redundantly sense the activities of these portions of the heart. It is contemplated that the microprocessor could choose which of the inputs 138a, b, d and e that would provide the most efficient sensing of the atrial and ventricular signals, or require the least power, from the power source 126, or most effectively breakup a cardiac arrhythmia. Further, the input 138f may be connected by the lead 21 to the reed switch 23, whereby the physician may dispose an external magnet to close the switch 23, whereby the microprocessor 100 is controlled to change or alter the program as stored in the memory 102. The multiplexer sequentially selects or steers one of the inputs 138a to f via conduit 118, which is input through an amplifier and analog digital converter 108 and the conducter 114 to the microprocessor 100. Multiplexing is used in order to reduce the hardware required for processing the analog information applied to the inputs 138a to f and also to reduce the power requirements for this function. Without the multiplexer 106, each of the inputs 138a to f would require its own individual scaling, amplifier and A/D converter 108. Thus, the use of the multiplexer 106 reduces the power drain applied to the power source 126 as well as reduces the circuitry to be incorporated within the pacemaker.

The microprocessor 100 applies via conduit 116 a scaler control signal to the scaling amplifier and A/D converter 108, whereby the scaling factor or gain of the amplifier within block 108 is controlled to accomodate for the various amplitudes of signals applied to the inputs 138a to f of the multiplexer 106. In this regard, it is understood that the output of the power source 126 could be illustratively in the order of 1.3 to 6 volts (initially), whereas the heart activity signals derived from the atrium and the ventricle would be illustratively in the order of 1 to 20 millivolts. The output of the amplifier and A/D converter 108 is a set of digital signals that are to be stored within the microprocessor 100 and in particular within the registers of the microprocessor 100. In a preferred embodiment of this invention, the microprocessor 100 could also be implemented by presently available low threshold CMOS technology, which implementation would provide a relatively low power drain upon the power source 126.

An essential element of the pacemaker 12 is the memory 102 which may include a non-volatile section, i.e., the read-only memory (ROM) portion 102a and a volatile portion, i.e., the random access memory (RAM) portion 102b. In the ROM or non-volatile portion 102a, the basic steps of each of a variety of pacing modes (or other processes) are stored. On the other hand, a variety of parameters or whole programs are stored in the RAM portion 102b, and at a later point in time could be reprogrammed dependent upon the changing condition of the patient. The memory 102 may be programmed at the time of manufacture, before implantation within the body of the patient, or via an external memory load interface 104, that is coupled by an RF frequency or acoustical link 105 to the memory 102. In an illustrative embodiment of this invention, a link as described in U.S. Pat. Nos. 3,833,005 and 4,066,086 (more fully identified above), may be readily adapted to be used as the interface 104. In particular, there is described a receiver filter for sensing bursts of RF pulses transmitted from an external transmitter, the bursts being coded in a manner to reprogram a program stored within the memory 102 or alternatively, to change a parameter stored within a memory location of the memory 102.

As will be explained in detail later, it is desired to maintain constant the energy of each stimulating pulse applied to the patient's heart, even though the voltage level of the power source 126, e.g., a battery, decreases with life. As indicated in FIG. 1, the multiplexer 106 periodically applies the battery voltage $V_s$ via the input 138c to the microprocessor 100, which under the control of a program stored in the memory 102 compares the measured voltage with various predetermined voltages stored in the ROM portion 102a or the RAM portion 102b whereby an adjustment in the pulse width of the stimulating pulse is made to maintain substantially constant the energy content, i.e., the area underneath the curve of the stimulating pulse.

Continuing with respect to FIG. 1, the control output signals of the microprocessor are applied via conduits collectively shown by numeral 131 to latch drivers 134 and by bus 132 to corresponding select switches 130, which provide appropriate pacemaker pulses via the leads 17 and 19 (or 29) to the atrium and ventricle of the patient's heart in accordance with the processes stored in the memory 102. In particular, conduit 131a is coupled to a first or ventricular driver (or amplifier) 134a, which is in turn coupled to its own set of bipolar/unipolar select switches 130a. It is understood that each of the driver amplifiers 134b, c and d is also associated with a similar set of select switches. For example, the output of driver 134b is connected to select switches 130b (not illustrated) for driving the patient's atrium via conduits 17a, 17b and 17c. It is also understood that the drivers 134a-134d may include voltage increase circuitry, e.g., doublers, triplers to raise the output voltage level to that necessary to effectively stimulate the heart tissue with a given power source voltage. The select switches 130 are under the control of signals derived from the microprocessor via bus 132 to selectively couple the output of the first driver 134a between selected of the outputs 19a, 19b, and 19c. In this regard it is understood that the switches 130 are coupled via the ventricular lead 19 which may take the form of a coaxial lead connected to a tip electrode via conducter 19a and to a ring electrode 19c, as more fully shown and explained, for example, in U.S. Pat. No. 4,010,758 by R. H. Rockland et al, as assigned to the assignee of this invention. In addition, there is provided a conductor 19b coupled to a plate formed of the metal container or can 13 in which the pacemaker 12 is encapsulated. In normal bipolar operation, the select switches 130 connect the negative and positive stimulating pulses via the conductors 19a and 19c of the coaxial lead to the tip and ring electrodes, respectively. If it is desired to pace in a standard unipolar mode, a negative voltage is applied via the conducter 19a to the tip electrode and a positive voltage via the conductor 19b to the plate, with the ring electrode not connected.

In this embodiment of this invention, the microprocessor 100 may take the form of a processor as manufactured by RCA Corporation under their designation "CDP 1802 COSMAC" microprocessor or the "CDP 1804 COSMAC" microprocessor (processing on-chip memory).

Referring now to FIG. 2, there is shown an illustrative embodiment of a low power A/D converter 308 corresponding to A/D converter 108 as incorporated into the pacemaker as shown in FIG. 1. As shown in FIG. 2, an analog voltage V(x) to be converted to digital form, is applied by input line 404 to a switch (S₁) 407 which is connected to an up or first position to apply the analog voltage V(x) to the input (V$_{IN}$) of a voltage control oscillator (VCO) 402, whose output is applied to the input of an accumulator counter 400. As indicated by the inputs to the counter 400, the accumulator counter 400 is capable of counting either "up" or "down" to provide an output via gate 414 to an input of an "N" output counter 412. A clock signal is applied via an input line 418 to control logic 408 and in particular to divide by N circuit 410, whose output is coupled to throw switch 407 to a second, down position, whereby a reference voltage is applied via conductor 406 to the input of the VCO 402, and at the same time a down command signal is applied via gate 418 to the down input of the accumulator counter 400, which then initiates a counting down mode. At the same time an output from the control logic 408 is applied to the reset of the "N" output counter 412.

The A/D converter 308 of FIG. 2 operates in the following fashion. An unknown voltage V$_X$ is applied to the VCO 402 via switch 407 for a fixed period of time T$_{up}$. During this time period T$_{up}$, accumulator counter 400 is counting up the output of the VCO 402. The accumulator counter 412 is acting very much like an analog integrator in that the count of the accumulator counter 400 is building up at a linear rate for a given voltage level of V$_X$.

Time T$_{up}$ is dependent upon the clock frequency applied to line 418 through the control logic 408 and the "N" counter 410. At the end of time T$_{up}$, switch S1 is disposed to its second position to connect the input of the VCO 402 to the reference voltage E$_{ref}$. Coincident with this switching to the reference voltage, the "A" accumulator counter 400 is placed in the down count mode. During this down count, circuitry is employed which examines when accumulator counter 400 has counted back to a predetermined count, e.g., zero. The time required to count the reference voltage back to zero is proportional to the average value of the input voltage, V$_X$. While the accumulator counter 400 is being counted back to zero the clock frequency, F$_{CLK}$ is counted by the "N" output counter 412. Counts accumulated in the "N" counter 412 are in digital form and are directly proportional to the initial unknown voltage, V$_X$. This results in a voltage to frequency conversion.

The basic equations for the operation of the A/D converter 308 are:

$$A_{up} = K_{VCO}\overline{V(x)}T_{up} \tag{1}$$

$$A_{DWN} = K_{VCO}E_{ref}T_X \tag{2}$$

Equations 1 and 2 give the up and the down count of accumulator counter 400 as a function of the unknown voltage and the reference voltage, and the length of time this voltage is applied to the VCO 402. The up count and the down count of the counter 400 are equal since the counter 400 is starting from zero and returning back to zero at the end of a cycle. Equating these two equations results in the elimination of the voltage controlled oscillator scale factor K$_{VCO}$ from the effect on output of the A/D conversion. Equation 3, which gives the output counter accumulated count N(X) as a function of the clock frequency F$_{CLK}$ and the length of time required to force the accumulator counter back to zero, that is, T$_X$, is reproduced as follows:

$$N(X) = T_X F_{CLK} \tag{3}$$

Equation 4, which gives the up count time, T$_{up}$, as a function of the "n" counter and the clock frequency, is as follows:

$$T_{up} = n/F_{CLK} \tag{4}$$

Equation 5, which shows that the output counter count N is proportional to n and the unknown voltage divided by the reference voltage, is as follows:

$$N(x) = n\frac{V(x)}{E_{ref}} \tag{5}$$

Equation 5 shows that the digital output count N(x) is independent of the clock frequency F$_{CLK}$, the strobe frequency, and of particular interest, the VCO scale factor. For example, if the unknown voltage, V$_X$ were two volts, the reference voltage were two volts and the n counter output was 64; at the end of each conversion output counter N would have a count of 64 in it. This particular characteristic of the A/D converter allows us to put a gain in series with switch S1 and the VCO 402 and essentially not effect the output count even if this gain were to change or be different from unit to unit provided that the gain were constant over one conversion cycle. In other words, as shown in FIG. 2, since a single VCO 402 is used to apply both the input analog voltage V(x) as well as the reference voltage E$_{REF}$, the scaling factor as imposed by the VCO 407 does not effect the digital output of the counter 412. Further, since the same clock signal $f_{CLK}$ is used to clock the first or accumulator counter 400 during the down period $T_X$, as well as to clock the "N" output counter 412 for the same period, the frequency of the clock signal $f_{CLK}$ does not effect the digital output of the counter 412 indicative of the amplitude of the input analog signal V(x). Thus, the clock used to supply the clock signal $f_{CLK}$ does not have to be of the high precision, relatively high power drain variety, but may be configured to impose a minimal drain upon the power source, i.e., the pacer's battery.

In FIG. 3, there is shown a detailed circuit implementation of the A/D converter 308 generally shown in FIG. 2. The input is applied to a bilateral switch taking the form of the switch 407 whose output is in turn applied to the VCO 402 contained in a phase lock loop circuit. In turn, the VCO output is applied to the accumulator counter 400 comprised of four up/down counters CD4029A. The clock frequency $F_{CLK}$ is applied with the strobe pulse via conductors 418 and 420 respectively to time the output of the accumulator 400 to the N output counter 412. A key part of the illustrative implementation of the A/D converter 308 is to design the control circuit 408, as shown in FIG. 2, to include a counter 409 in the form of a four-bit ring counter. This counter 409 forces the A/D converter 308 into one and only one of four possible modes, corresponding to its four output states 0, 1, 2 and 3. These four modes of operation of the A/D converter 308 as shown in FIG. 3, are: (1) wait; (2) preset; (3) up count; and (4) down count.

The wait mode is a resting mode for the A/D converter 308 in which the VCO 402 is turned off, the unknown and reference voltages are disconnected via bilateral switch 407 from the VCO 402, and the last converted digital word is resting in counter 412 as a digital, parallel eight bit word. The converter 308 rests in this wait mode until it receives a strobe pulse which drives it to the preset mode. Very low power is drawn by the A/D converter 308 while in the wait mode.

The preset mode follows the wait mode and is used for presetting the accumulator comprised of counters 400a, 400b, and 400c, to a binary word of one via a jam input. Counter 412 is reset during the preset mode. The maximum time the preset mode exists is one-half of a clock period.

During the up mode, output 3 of the divider 409 is energized to logic 1 which forces accumulator counters 400a, 400b and 400c to count in the up mode. During this mode bilateral switch S1 directs the unknown analog input to the input of the VCO 402. Also "N" counter 410 begins to time the length of time the unknown voltage is applied by counting the reference clock frequency to the preprogrammed count which will bring the output of AND gate 425 to a logic one. During this mode, counts are accumulated in the counters 400a, 400b and 400c. When the output of AND gate 425 reaches a logic one indicating the up count time period has been reached, its inputs are both logic one and a command to advance the ring counter 409 is applied to the pulse stretcher gate 427. At the next clock pulse reaching logic one drives ring counter 409 to the next state which is the down count.

A down count mode is established by energization of the output 7 of the ring counter 409 to a logic one. This condition forces the accumulator counter 400 to count down. Also the reference voltage is applied to the voltage controlled oscillator 402. Also the clock frequency is directed to the input of N counter 412. Thus as the counts are driven out of accumulator counters 400a, 400b, and 400c, clock pulses are being accumulated in N counter 412. When the accumulator counter chain has driven to logic zero in all states, the output of AND gate 429 rises to logic one and forces the ring counter 409 to its wait mode through the pulse catching network described previously. The completion of this cycle results in unknown input voltage V(x) being digitized and held in output counter 412 with the scale factor as described above.

The A/D converter 308 as shown in FIGS. 2 and 10 is particularly designed to be incorporated within a cardiac pacer, as shown in FIG. 1. As indicated above, it is significant to incorporate within the pacer, circuitry that will impose a minimum drain upon the pacer's power source, e.g., its battery. To this end the circuitry as illustratively shown in FIG. 3 may be implemented by CMOS technology. Secondly, as described above, the oscillator 402 is only energized to provide an output during those times in which an input analog signal V(x) is to be digitized; at other times, the VCO 402 is deenergized. The energization of the VCO 402 is under the control of the control circuit 408 and in particular of the ring counter 409. Thirdly, the A/D converter 308 may be adjusted by incorporating different values of "n" within the counter 410, whereby the A/D converter 308 is adapted to sense input voltages of varying amplitudes. In the various embodiments of pacemakers employing this invention, it is contemplated that it would be desired to convert the relatively large voltage $V_S$ of the battery, as well as the relatively small voltage signals as derived from the patient's ventricle and atrium. As shown in FIG. 3, the preselected up time period $T_{up}$ is determined by the value of "n" as set in the "n" counter 410. The value of "n" may in one illustrative embodiment of this invention be set by connecting one of the plurality of outputs Q4, Q5, Q6, and Q7 of the N counter 410. It is contemplated that a switch circuit (not shown) could be incorporated between one of the outputs of the counter 410 and the AND gate A9, whereby the value of "n" could be placed under the control of the microprocessor 300, as shown in FIG. 7A. In addition, a programmable counter, as are well known in the art, could be substituted for the present counter 410 whereby a suitable binary word could be stored therein to be varied under the control of the microprocessor. Thus, the value of "n" could be varied dependent upon which input analog signal was to be converted into digital form. The value "n" is varied dependent upon the amplitude of the contemplated input voltage V(x), with larger values of "n" being selected for smaller amplitudes. As a practical matter, it is desired to achieve a count within the output counter 412 close to its known capacity, whereby the maximum resolution for an input signal of given amplitude is assured. Thus, a single analog digital converter 308 may be used for different input signals of varying amplitude, ensuring the precision of the binary output signal by varying the value of "n".

Numerous changes may be made in the above-described apparatus and the different embodiments of the invention may be made without departing from the spirit thereof; therefore, it is intended that all matter contained in the foregoing description and in the accompanying drawings shall be interpreted as illustrative and not in a limiting sense.

What is claimed is:

1. Apparatus for converting analog input signals to corresponding digital output signals, said converting apparatus comprising:
   (a) oscillator means having an input for providing a first output signal whose frequency is dependent upon the signal applied to its input;
   (b) reference means for generating a reference signal;
   (c) switch means coupled to said input of said oscillator means and disposable from a first position wherein switch means applies said analog signals to said input of said oscillator means to a second position wherein said switch means applies said reference signal to said input of said oscillator means;
   (d) first counter means coupled to receive said first output signal and comprising mode control means for causing said first counter to operate in a first mode to count up and in a second mode to count down in accordance with the frequency of said first output signal to provide a second output signal indicative that the count of said first counter has reached a predetermined count;
   (e) second counter means coupled to receive said second output signal, for providing a corresponding third digital output signal indicative of the count of said second counter;
   (f) clock means for providing a clock signal to said second counter;
   (g) control means coupled to receive said clock signal and for providing a control signal after receipt of a selected number N of oscillations of said clock signal, said switch means responsive to said control signal to be disposed from its first position to its second position, said mode control means of said first counter means responsive to said control signal to terminate said first counter operating in its first mode at which time the count reached by said first counter is a first count indicative of said analog input signal and to initiate its second mode to count down from said first count, said second counter means comprising means responsive to said control signal to initiate counting the oscillations of said clock signal and responsive to said second output signal indicating that said predetermined count has been reached by said first counter to terminate counting the oscillations of said clock signal, to provide said third digital output signal indicative of said analog input signal.

2. The converting apparatus as claimed in claim 1, wherein said control means includes third counter means for counting "n" oscillations of the clock signal and thereafter providing the control signal, said third counter means includes means for variably setting the value of "n".

3. The converting apparatus as claimed in claim 1, wherein said control means comprises means for receiving a strobe signal and responsive to said strobe signal for activating said oscillator means.

4. The converting apparatus as claimed in claim 3, wherein said responsive means comprises a ring counter enabled in response to said strobe signal and providing a first counter output signal to said switch means to cause said switch means to apply said analog input signal to said oscillator means following said strobe signal, until generation of said control signal and providing a second counter output signal to said switch means to cause said switch means to apply said reference signal to said oscillator means following said control signal.

5. The converting apparatus as claimed in claim 1 wherein said apparatus comprises C-MOS circuitry.

* * * * *